US007101554B2

(12) United States Patent
Niklasson

(10) Patent No.: US 7,101,554 B2
(45) Date of Patent: Sep. 5, 2006

(54) PICORNAVIRUSES, VACCINES AND DIAGNOSTIC KITS

(75) Inventor: Bo Niklasson, Stockholm (SE)

(73) Assignee: Microtus AB, Kalmar (SE)

( * ) Notice: Subject to any disclaimer, the term of this patent is extended or adjusted under 35 U.S.C. 154(b) by 0 days.

(21) Appl. No.: 09/147,801

(22) PCT Filed: Sep. 9, 1997

(86) PCT No.: PCT/SE97/01515

§ 371 (c)(1),
(2), (4) Date: Mar. 11, 1999

(87) PCT Pub. No.: WO98/11133

PCT Pub. Date: Mar. 19, 1998

(65) Prior Publication Data

US 2003/0044960 A1    Mar. 6, 2003

(30) Foreign Application Priority Data

Sep. 11, 1996  (SE) ................................. 9603305

(51) Int. Cl.
*A61K 39/125* (2006.01)
*C12Q 1/70* (2006.01)
*C07K 14/085* (2006.01)
*C07K 16/10* (2006.01)

(52) U.S. Cl. ............................... 424/186.1; 424/216.1; 435/235.1; 435/5; 530/300; 530/350; 530/387.9; 530/388.3; 530/389.4

(58) Field of Classification Search ............... 530/350, 530/389.4, 388.3, 300, 387.9; 435/5, 235.1; 424/186.1, 216.1
See application file for complete search history.

(56) References Cited

U.S. PATENT DOCUMENTS 5,229,111 A    7/1993  Palmenberg et al. ..... 424/205.1

OTHER PUBLICATIONS

Niklasson et al., A New Picornavirus Isolated from Bank Voles (*Clethrionomys glareolus*). Virology 255:86-93, 1999.*
Rueckert, Roland R. Picorrnaviridae: the viruses and their replication. Fields Virology, 3rd edition, ed. B.N. Fields et al, Lippincott-Raven Publishers, Philadelphia, 1996, pp. 609-654.*
Melnick, Joseph L. Enteroviruses: polioviruses, coxsackieviruses, echoviruses, and newer enteroviruses. Fields Virology, 3rd edition, ed. B.N. Fields et al, Lippincott-Raven Publishers, Philadelphia, 1996, pp. 655-712.*
Hypia et al. Proceedings of the National Academy of Sciences USA 89:8847-8851, 1992.*
AAM46801 (Genbank AF327922.1) [online][retrieved Jan. 14, 2005] Retrieved from NCBI Entrez Protein, from the Internet <http://www.ncbi.nlm.nih.gov/entrez/viewer.fcgi!db=protein&val=21309880>.*
Johansson et al (Journal of Virology 76:8920-2930, 2002).*
Lindberg et al (Virus Research 85:61-70, 2002).*
Hughes (Infection, Genetics, and Evolution 4:143-152, 2004, abstract only cited).*
Hyypiä et al., Proc. Natl. Acad. Sci., 89: 8847-8851 (1992).
Jun et al., Journal of General Virology, 76: 2557-2566 (1995).
Dan et al., Exp. Anim., 44(3): 211-218 (1995).
Tolbert et al., Proc. Soc. Exp. Biol. Med., 205(2): 124 (1994).
Dialog Information Services, file 34, SciSearch, Dialog accession No. 14364904.
Dialog Information Services, file 154, MEDLINE, Dialog accession No. 08478765.
Dialog Information Services, file 154, MEDLINE, Dialog accession No. 08518839.
Dialog Information Services, file 154, MEDLINE, Dialog accession No. 06649814.
Dialog Information Services, file 34, SciSearch, Dialog accession No. 14364904, 1995.
Dialog Information Services, file 154, MEDLINE, Dialog accession No. 08478765, 1994

(Continued)

*Primary Examiner*—Mary E. Mosher
(74) *Attorney, Agent, or Firm*—Kohn & Associates, PLLC; Kenneth I. Kohn

(57) ABSTRACT

A new group of picornaviruses is disclosed. The picornaviruses of the invention comprise in the non-coding region of their viral genome a nucleotide sequence which corresponds to cDNA sequence (I) or homologous sequences having at least 75% homology to the SEQ ID NO:1, and they cause mammalian disease. Further aspects of the invention comprise a protein corresponding to a protein of the picornaviruses, antiserum or antibody directed against a protein of the picornaviruses, antigen comprising a protein of the picornaviruses, diagnostic kits, vaccines, use of the picornaviruses in medicaments, particularly for the treatment or prevention of Myocarditis, Cardiomyopathia, Guillain Barré Syndrome, and Diabetes Mellitus, Multiple Sclerosis, Chronic Fatique Syndrome, Myasthenia Gravis, Amyothrophic Lateral Sclerosis, Dermatomyositis, Polymyositis, Spontaneous Abortion, and Sudden Infant Death Syndrome, and methods of treatment of diseases caused by the picornaviruses.

```
SEQ ID NO: 1 (Ljungan 87-012)                           (I)
AGTCTAGTCT TATCTTGTAT GTGTCCTGCA CTGAACTTGT    50
TTCTGTCTCT

GGAGTGCTCT ACACTTCAGT AGGGGCTGTA CCCGGGCGGT   100
CCCACTCTTC

ACAGGAATCT GCACAGGTGG CTTTCACCTC TGGACAGTGC   150
ATTCCACACC

CGCTCCACGG TAGAAGATGA TGTGTGTCTT TGCTTGTGAA   200
AAGCTTGTA

AAATCGTGTG TAGGCGTAGC GGCTACTTGA GTGCCAGCGG   250
ATTACCCCTA

GTGGTAACAC TAGC
```

9 Claims, No Drawings

OTHER PUBLICATIONS

Dialog Information Services, file 154, MEDLINE, Dialog accession No. 08518839, 1995

Dialog Information Services, file 154, MEDLINE, Dialog accession No. 06649814, 1990.

* cited by examiner

PICORNAVIRUSES, VACCINES AND DIAGNOSTIC KITS

FIELD OF INVENTION

The present invention relates to new picornaviruses, proteins expressed by the viruses, antisera and antibodies directed against said viruses, antigens comprising structural proteins of said viruses, diagnostic kits, vaccines, use of said viruses, antisera or antibodies and antigens in medicaments, and methods of treating or preventing diseases caused by said viruses, such as Myocarditis, Cardiomyopathia, Guillain Barré Syndrome, and Diabetes Mellitus, Multiple Sclerosis, Chronic Fatigue Syndrome, Myasthenia Gravis, Amyothrophic Lateral Sclerosis, Dermatomyositis, Polymyositis, Spontaneous Abortion, and Sudden Infant Death Syndrome.

BACKGROUND OF THE INVENTION

Recently, a sudden death syndrome among Swedish orienteers has been observed. Of approximately 200 elite orienteers six died in myocarditis during 1989–1992 (1). Orienteering, aiming to find the fastest/shortest way between several checkpoints and often in forested areas, is exceptional with respect to environmental exposure. Thus it has been speculated, that the sudden deaths syndrome among orienteers is caused by a vector borne (rodent or arthropod) infectious agent.

It has now been shown in an epidemiological study that the incidence of deaths in myocarditis in northern Sweden tracked the 3–4 year population fluctuations (cycles) of bank voles (*Clethrionomys glareolus*) with one year time lag. Previously, it has been shown that cardioviruses, with rodents as their natural reservoir, can cause Guillain Barré Syndrome (GBS) in man, Diabetes Mellitus (DM) in mice and myocarditis in several species including non-human primates.

In addition to death in myocarditis it is also shown in the epidemiological study that the number of patients diagnosed with Guillain Barré Syndrome (GBS), and Diabetes Mellitus (DM) in northern Sweden tracked the 3–4 year population fluctuations of bank voles with different time delays.

Sven Gard and co-workers studied antibody prevalence to encephalomyelitis virus (EMCV) in Swedish normal population in the early 1950th (2). These studies found a surprisingly high antibody prevalence rate by hemagglutination inhibition test but no sera could be confirmed by neutralization test. These results were found puzzling at the time but could be explained by the presence of one or several related picornaviruses circulating in Sweden.

The fact that enterovirus have a large number of members and cardiovirus only two possibly three could reflect the true diversity of the two genus or only be the result of the amount of effort made to isolate new viruses from rodents as compared to isolating new enteroviruses from humans.

The Picornavirus family is presently divided into five genera (aphto-, entero-, hepato-, rhino-, and cardioviruses) (3). This taxonomy was initially based on morphological, physiological and serological properties as well as on the pathogenicity of the viruses. More recently, however, viruses have been characterized based on their genome sequence since it has been established that sequence data to a large extent coincide with the characterisation properties used previously (4,5).

The prototype virus in the cardiovirus genus is Theiler's murine encephalomyelitis virus (TMEV). Another member in this genus is encephalomyocarditis virus (EMCV). Vilyuisk virus, isolated from patients in Russia with degenerative neurological disease, is serologically related to TMEV but presently under consideration for being included as a third distinct member of the cardiovirus genus (6).

In nature, cardioviruses have a geographically widespread distribution and a large number of susceptible hosts with rodents as their natural reservoir. In addition to rodents, EMCV has been isolated from domestic pigs, elephants, lions, non human primates and man (7,8,9). Infection with TMEV and EMCV have provided excellent animal models for inducing myocarditis, DM and different neurological disorders such as demyelinating diseases resembling multiple sclerosis in mice (10–16). Other neurological or muscular disorders in which an infection is suspected to be the triggering factor and in which there is also an autoimmune component are Cardiomyopathia, Multiple Sclerosis (MS), Chronic Fatigue Syndrome (CFS), Myasthenia Gravis (MG), and Amyothrophic Lateral Sclerosis (ALS). It has never been established, however, that cardiovirus is a significant human pathogen, as disease in man most often has been described in case reports or as infection measured in sero-epidemiological surveys (7–17).

Thus, there may be other not yet identified picornaviruses circulating in the wild rodent population and occasionally infecting humans resulting in Myocarditis, Cardiomyopathia, Guillain Barré Syndrome, and Diabetes Mellitus, Multiple Sclerosis, Chronic Fatigue Syndrome, Myasthenia Gravis, Amyothrophic Lateral Sclerosis, Dermatomyositis, Polymyositis, Spontaneous Abortion, and Sudden Infant Death Syndrome, in genetically susceptible individuals.

The epidemiological link between important human diseases and small rodent abundance and what is previously known about picornavirus/cardiovirus motivated attempts to isolate novel picornaviruses from small rodents.

DESCRIPTION OF EXPERIMENTAL WORK AS BASIS FOR THE INVENTION

Trapping of Animals

Small rodents were trapped at several locations in northern Sweden and transported live to the Swedish Institute for Infectious Disease Control in Stockholm, Sweden. Species, date and location of trapped animals were recorded. Animals were bled using ether anaesthesia and killed. Organs were immediately removed and stored at −70° C. until tested for presence of virus. A total of 53 *Clethrionomys glareolus* and 28 *Microtus agrestis* were tested for virus isolation.

Virus Isolation

The isolation technique used in the present study was different from what is most often used. The cells used for isolation were kept for a minimum of two weeks and virus growths were detected by both CPE (cytopathogenic effect) and by staining the cells by a large number of human sera using IFT (immunofluorescense test). None of the new viruses presented herein would have been isolated using routine procedure for detecting cardioviruses/picornaviruses. They grow to lower titer and CPE develops slowly.

Saliva mixed with lung homogenate and faeces were analyzed separately from each animal. The material was inoculated into T25 flask of confluent BHK-21 cells. Cells were blind passed twice a week during two weeks. At the end of this period or earlier if signs of CPE occurred, cells were removed from the T25 flask by a rubber policeman, placed onto 10-well spot slides, air dried and acetone fixed. The cells were then stained with panels of human sera including 5 multiple scleroses patients, 5 patients recently diagnosed with DM and 5 athletes dying in myocarditis and bled at autopsy. All T25 flasks (saliva-lung and faeces separately) were tested individually by IFT using the complete panel of human sera at a 1:10 dilution.

Cells showing positive reaction by IFT using the human serum panels were selected for further analysis. This included inoculation intracerebrally into 1 day old suckling mice, serological characterisation and sequence analysis.

Antisera and Serological Procedures

Antisera to the virus isolates were raised in mice (NMRI), and Guinea Pigs (Dunkin Hartley). The animals were injected with a cell culture supernatant from (BHK-21 cells) intraperitoneally and serum collected 4–6 weeks later.

reimmunization sera were tested individually while postimmunization sera were pooled from all infected animals.

An indirect immunoflouresence test (IFT), as described previously (18,19) was used to test antibody titres in immunized animals. Briefly, spot slides were prepared by incubating virus on Green Monkey Kidney (GMK) cells for 6–10 days. At sign of discrete CPE cells were removed from the flask by a rubber policeman and put onto the microscope slides, air dried, and fixed in cold (4° C.) acetone and stored at −70° C. The titer was determined by incubating serum diluted in PBS in the slides at 37° C. for 1 hour in a moist chamber, followed by a FITC conjugate (F(ab')$_2$ fragment of goat anti human IgG γ-chain specific, Sigma Immuno Chemicals (F-1641) or Rabbit anti mouse immunoglobulins Daco (F0313)) incubated as above.

Antibody titers to the viruses were determined by a modification of the Plaque reduction neutralization test (PRNT) as described by Earley et al (20). In the test, sera were serially diluted four-fold and mixed with an equal volume containing 80–100 plaque-forming units (pfu) of virus per 50 μl. The mixtures were then incubated at 37° C. for 60 minutes, and 50 μl subsequently inoculated into each of 2 wells of a tissue culture plate containing confluent Vero cell monolayer. After adsorption for 60 minutes at 37° C. the wells were overlaid with 0.5 ml of a 42° C. mixture of 1 part 1% agarose and 1 part 2× basal Eagle's medium with Earle's salts, 17 mM Hepes buffer, 8% heated fetal calf serum, 100 U/ml penicillin, 100 μg streptomycin. The tissue culture plates were incubated at 37° C. in a humidified 5% $CO_2$ atmosphere for 3–7 days. A second overlay (0.5 ml) containing neutral red stain (1:9000) was then applied and plaques were enumerated the following day. The plaque numbers were linearly extrapolated to 2-fold dilutions. An 50% reduction of plaques was used as the criterion for virus neutralization titers.

Electron Microscopy

Cell culture media or brain tissue homogenates were examined by negative contrast electron microscopy (EM). A 10 μl droplet was incubated on Formvar/carbon-coated grids for one minute or alternatively, 0.5 ml samples were centrifuged for 30 minutes at 20,000×g to remove cell debris and finally the supernatants were pelleted directly onto grids in a Beckman Airfuge for 10 minutes at 160,000×g. Grids were stained with 2% phosphotungstate acid (pH 6.0) and examined in a Philips CM 100 electron microscope at a magnification of at least 46,000.

Sequence Data

The isolates 87-012, 174F and 145SL were grown on the human lung carcinoma line A549 in 1600 cm$^2$ roller bottles. Full CPE was observed after 5–10 days. Supernate was filtered through 0.45 μM cellulose acetate filters (Costar) and the virus was pelleted at 20,000 g for 20 h at 4° C. RNA was isolated from the virus containing pellets using acid guanidinium thiocyanate as described (Chomczynski and Sacchi). Synthesis of cDNA was performed under standard conditions using 1 μg of RNA, AMV reverse transcriptase (Boehringer-Mannheim) and random 14 mer oligonucleotides as primers in a 20 μL reaction. Fragments of the viral 5'UTR were amplified using cardiovirus specific consensus primers: (sense) 5'-GGCCGAAGCCGCTTGGAATA-3' (SEM) [SEQ ID NO. 21] and (antisense) 5'-GTGGCTTTTGGCCGCAGAG-3' (ATVEM) [SEQ ID NO. 22], both primers modified after the EMCV2 and EMCV1 primers previously reported (Jongen et al. 1993. Ann. Reum. Dis. 52: 575–578). Cardiovirus sequences were from Dr a. Palmenberg (personal communication). Amplification conditions were 30 cycles at: 94° C., 30 sec., 50° C., 30 sec, 72° C., 2 min. The amplified fragments were cloned into the pCRII T-vector (In-Vitrogen). The cloned viral sequences were sequenced using A Taq polymerase FS cycle sequencing kit and data was collected on a ABI Prism 310 sequencing machine using M13–21 and M13 reverse primers (Perkin-Elmer). A 1.8 kb fragment extending from the 5'-UTR into the viral polyprotein sequences was obtained by PCR (polymerase chain reaction) amplification of cDNA from the 145SL isolate. The primers were: (sense) 5'-ACAGTGCATTCCACAC-3' (SLJU1) [SEQ ID NO. 23] OR 5'-CCGCTCCACAATAGA-3' (SLJU2) [SEQ ID NO. 24] and (antisense) 5'-GATCTCAGAC-3' (primer 118) [SEQ ID NO. 25]. The SLJU1 and SLJU2 primers are located immediately adjacent to one another and were chosen as consensus primers for the Ljungan isolates of the invention with as little homology as possible to the EMCV and TMEV groups of viruses. The amplification conditions were 30 cycles at: 94° C., 30 sec., 42° C., 1 min , 72° C. 2 min. The antisense primer 118 [SEQ ID NO. 25] yielded similarly sized PCR products with either the SLJU1 [SEQ ID NO. 23] or SLJU2 [SEQ ID NO. 24] as sense primers, but none of the primers yielded PCR fragments when used alone. The sequence of the primer 118 [SEQ ID NO. 25] was previously published (Bauer, D., et al. 1993. Nucl. Acids Res. 21: 4272–4280). The obtained 1.8 kb PCR fragment was cloned and sequenced as described above.

Results of Experimental Work

Three virus isolates were selected based on reaction with the human serum panels and showing a size and structure compatible with a picornavirus on EM. The first isolate was named Ljungan 87-012. Ljungan is a river in Medelpad county, Sweden where the animals were trapped.

The second and third isolate were designated Ljungan 174F and Ljungan 145SL, respectively.

All three isolates came from *C. glareolus*.

All three isolates killed suckling mice in 3–5 days.

The titer in mouse brain was $10^9$ (approximately) while the cell culture titer was only $10^5$ (approximately).

Electron Microscopy

Virus particles, 27 nm in diameter, were spherical with the surface almost featureless and they appeared single or in small aggregates. In rare cases the stain penetrated the particles which made them look like empty shells.

Serological Results

It was found after testing a number of different cell lines the Green Monkey Kidney cells were most suitable for making IFT drop slides for serology. The cross IFT data using mouse sera are seen in Table 1.

TABLE I

Cross-IFT using virus infected GMK cells. Immune mice were titrated using 4 fold dilutions starting at a 1:10 dilution.

| Antisera | VIRUS | | |
|---|---|---|---|
| | 87-012 | 174F | 145SL |
| 87-012 | 2560 | 160 | <10 |
| 174F | 160 | 160 | <10 |
| 145SL | 40 | 40 | 640 |

PRNT (plaque reduction neutralization test) data, preliminary results. Rabbit sera against TEMV and EMCV with a titer of 1:160 homologous had a titer less than 10 to the three isolates. Several attempts to make antisera with neutralizing titer in bank voles, mice, rabbits and guinea pigs have failed. All animals made high titer antibodies by IFT but no by PRNT. Bank voles failed to make IFT antibodies.

Sequence Data

Sequences from 5'UTR and polyprotein gene of Ljungan virus isolates.

Cardiovirus consensus primers yielded a product of 303 bp for the three isolates 87-012, 174F and 145SL, compared to 284 bp for EMC virus. The fragment amplified was located immediately after the end of the poly C tract in EMC virus. PCR products specific for the Ljungan isolates were only obtained when the reannealing temperature was 50° C., and not at 58° C., which was optimal for obtaining products from EMC virus CDNA. The subsequent sequence analysis revealed that the ATVEM primer was mismatched at 4 internal positions, explaining this difference in reannealing temperature. An alignment of the 5'UTR sequences for the three Ljungan isolates, EMCV and Vilyuisk virus (Table 2) shows a greater similarity between EMCV and Vilyuisk virus than between either of the two and the Ljungan isolates. It also demonstrates that each Ljungan isolate is distinct from the other by a number of nucleotide changes. The 174F and 145SL are similar to the isolate 87-012. The sequence homology between 174F and 87-012 was at most 95% (three undetermined bases in the sequence) while the homology between 87-012 and 145SL was 91%.

The strategy chosen for obtaining additional PCR fragments from the Ljungan virus isolates was a modification of a technique for detecting differentially expressed mRNAs (Bauer, D., et al. 1993. Nucl. Acids Res. 21: 4272–4280). As a test for this strategy, cDNA from the Ljungan 145SL isolate was amplified using the conditions above, using either the SLJU1 [SEQ ID NO. 23] or the SLJU2 [SEQ ID NO. 24] primer as a sense primer and one of twenty 10-mer oligonucleotides of randomly chosen sequence as "antisense" primer.

If the PCR products obtained with the SLJU1 [SEQ ID NO. 23] or SLJU2 [SEQ ID NO. 24] primers and a specific 10-mer were similarly sized, and none of the primers yielded a product of this size when used alone in the PCR reaction, the fragment obtained was isolated and cloned. Only one combination of primers satisfied this criterion, namely the SLJU1 [SEQ ID NO. 23] or SLJU2 [SEQ ID NO. 24] primers in combination with the 118 10-mer oligonucleotide, [SEQ ID NO. 25], which yielded a 1.8–1.9 kb PCR product. Of this fragment, 819 bp were sequenced from the 3' end. This sequence contained an open reading frame (ORF) of 663 bp in the sense of the viral polyprotein. This ORF was used to search in the Swiss protein data bank using the BLITZ search service from EMBL with the default search parameters. The top 10 scores were picornavirus polyprotein sequences, including 8 cardiovirus sequences. Homology was found over 188 a.a. The relatedness of this segment of the viral polyprotein to previously sequenced cardioviruses is shown in Table 3. A comparative alignment of all cardioviruses was made available to us by Dr. A. Palmenberg. In Table 3, the sequence of TMEBeAn was arbitrarily taken as the index strain. For the 12 remaining cardioviruses in the alignment, only differences in amino acid sequence are shown. The alignment of the Ljungan 145SL sequence is similarly represented at the top. Since the BLITZ search algorithm takes into account identical as well as similar amino acids, the latter have been indicated by small type, while differences to TMEBeAn is in capitals as for the other strains in the alignment.

In conclusion, the above presented data for the Ljungan isolates are characteristic for the 3 viruses but yet incomplete. However, the comparison of cloned sequences from both a highly conserved part of the 5'-untranslated region of cardioviruses and coding sequences for the viral capsid proteins of one isolate (Ljungan 145SL) clearly show that the Ljungan viruses are related to the cardioviruses, but are more distant relatives than any previously identified cardiovirus. While the amino acid homology (identical amino acids) of the viruses within the Theiler group is 96–97%, the homology to Vilyuisk virus is about 83%, and the EMC viruses are 67–74% homologous to TMEBeAn, the Ljungan 145SL has only about 32% identical amino acids to TMEBeAn. Even if homology is taken as identical and similar amino acids, this measure of relationship would still amount to only 50% between Ljungan 145SL and TMEBeAn (the corresponding figure would be 79–83% between EMC and TMEBeAn).

Alignment of Sequences

Table 2 shows an alignment of three Ljungan virus isolates (1. 87-012, 2. 174F, 3. 145SL) [SEQ ID NO. 1, 2 and 3 respectively] with published cardiovirus sequences (4. TMEBeAn, 5. Vilyuisk, 6. EMCV) [SEQ ID NO. 5, 6 and 7 respectively]. The aligned sequence starts 29 nt 3' of the end of the poly-C tract in EMCV, and the sequence corresponds to nt 557–808 (approximately) in the different viral genomes. Inserted spaces in the sequences are indicated by a period (.).

TABLE 2

```
1.  AGTCTAGTCTTATCTTGTATGTGTCCTGCACT..GA..ACTTGTTTCTGT
2.  AGTCTAGTTTCATTCTGTGTGTGTTTGGCACT..GA..AATTATTTCTGT
3.  AGTTTGGTTCTCTCTTGAGTGTGTTTTGTGTT..AG..CATAATTTCTGT
4.  TGACAGG.GTTATTTTCACC.TCTTCTT..TTCTACTCCACAG.TG.T.T
5.  TGACAGG.GTTATTTTCACC.TCTTCTCTCTTCTACTTCATAG.TG.T.T
6.  AGGCCGGTGTGCGTTTGTCTATATGTTATTTTCCAC..CATA.TTGCCGT
```

TABLE 2-continued

```
1. CTCTGGAGTGCTCTACACTTCAGTAGGGGCTGT.A.CCCGGGCGGTCCCA
2. CTCTGGGGTGCTTTACACTTCAGTAGGGGCTGT.A.CCCGGGCGGTCCCA
3. CTCTAGAGTGCTTTACACTCTAGTAGGGGCTGT.A.CCCGGGCGGTCCCA
4. CT.A.........TACTGTG..GAAGGGTATGTGT....TGCCCCTTCCT
5. CT.A.........TACTATG.AA.AGGGTATGTGT..C..GCGCCTTCCT
6. CT.T.......TTGGCAATGT.G.AGGGCCCG.GAAACCTGGCCCTGTCT

1. CTCTTCACAGGAATCTGCACAGGTGGCTTTCAC.CTCTGGACAGTGCATT
2. CTCTTCACAGGAATNTGCACAGGTGGCTTTCAC.CTCTGGACAGTGCATT
3. CTCTTCACAGGAATCTGCACAGGTGGCTTTCAC.CTCTGGACAGTGCATT
4. .TCTTGGAGAACGT..GCGCGGCGGTCTTTCCGTCTCTCGACAA.GCGC.
5. .TCTTGGAGAACGT..GCGTGGCGGTCTTTCCGTCTCTCGAAAAACG..T
6. .TCTTGACGAGCAT.T.CCTAGGGGTCTTTCCC.CTCTCGCCAAAGGAAT

1. CCACACCCG.C.TCCACGGTAGAAGATGATGTGTCTTTGCT..TGTGA
2. CCACACCCG.C.TCCACAGTAGAAGATGATGTGTCTTTGCT..TGTGA
3. CCATACCCG.C.TCCACAATAGAAGATGATGTATATCTTTGTT..TGTGA
4. GCGT..GCAACATACAGAGT.AACG.CGAAGAA.AGCA..GTTC.TC.GG
5. GCGT..GCGACATGCAGAGT.AACG.CAAAGAA.AGCA..GTTC.T.TGG
6. GCA.A.G.GTC.TGTTGAAT.GTCG.TGAAGGA.AGCA..GTTCCTCTGG

1. AAA.GCTT...GTGAAAATC........GTGTGTAGGCGTAGCGGCTACT
2. AAA.GCTT...GTGAAAATC........GTGTGTAGGCGTAGCGGNTACT
3. AAT.GCT.CA..TGAA.A.C......GTGTGTGTAGGCGTAGCGGCTACT
4. TCTAGCT.CTAGTGCCCA.CAAGAAAACAGCTGTAG.CG.ACCA.C.ACA
5. TCTAGCT.CTGGTGCCCA.CAAGAAAACAGCTGTAG.CG.ACCA.C.ACA
6. AA..GCTTCT..TGAAGA.CAA.ACAACGTCTGTAG.CG.ACC..CT..T

1. TGAGTGCCAGCGGATTACCCCTAGTGGTAACACTAGC [SEQ ID NO: 1]
2. TGAGTGCCAGCGGACNACCCCTAGTGGTAACACTAGC [SEQ ID NO: 2]
3. TGAATGCCAGCGGAACCCCCCTAGTGGTPACACTAGC [SEQ ID NO: 3]
4. ..AAGGC.AGCGGAACCCCCTCCTGGTAACAGGAGC  [SEQ ID NO: 5]
5. ..AAGGC.AGCGGAAACCCCCTCCTGGTAACAGGAGC [SEQ ID NO: 6]
6. TGCAGGC.AGCGGAACCCCCCACCTGGCGACAGGTGC [SEQ ID NO: 7]
```

In this region of the viral genome, Ljungan 174F has 94% homology to Ljungan 87-012 (here taken as the indicator strain for comparisons), and Ljungan 145SL has 91% homologous residues to Ljungan 87-012. The TMEBeAn strain has 69%, Vilyuisk has 68% and EMCV has 68% homologous residues to Ljungan 87-012. Using the same criteria for calculating the homology, EMCV has 85% homology to TMEBeAn.

Table 3 shows alignment of cDNA sequences from the polyprotein coding sequences of the Ljungan 145SL isolate [SEQ ID NO. 4] to the amino acid sequences of sequenced cardioviruses in the comparative alignment compiled by Dr. A. Palmenberg (personal comm.). Table 3 show the alignment of Ljungan 145 SL [SEQ ID NO. 4], TMEBeAn [SEQ ID NO. 8], TMEGd7 [SEQ ID NO. 9], TMEGd7b [SEQ ID NO. 10], TMEDa [SEQ ID NO. 11], Vilyuisk [SEQ ID NO. 12], EMCBd [SEQ ID NO. 13], EMCBc [SEQ ID NO. 14], EMCDd [SEQ ID NO. 15], EMCDc [SEQ ID NO. 16], EMCDv1 [SEQ ID NO. 17], EMCR [SEQ ID NO. 18], MengoM [SEQ ID NO. 19] and Mengo37a [SEQ ID NO. 20]. The TMEBeAn strain was arbitrarily taken as the indicator strain, while the amino acids of the remaining strains are shown only if they differ from the indicator strain. For the Ljungan 1455L isolate, similar, but non-identical amino acids are indicated in small type. The amino acid homology between Ljungan 1455L and other cardioviruses was established screening the entire Swiss Protein Data Bank using the BLITZ search algorithm with standard search parameters.

TABLE 3

| | |
|---|---|
| Ljungan | 464 480 525 |
| 145SL | K--m-iArm-sVyK-ERTEPGGTNG--QWshtHSPInW-.fDGGiHLED-P-..-LFsSCy- |
| TMEBeAn | SDLLELCKLPT.FLGNPNTNNKRYPYFSATNSVPATSMVDYQVALSCSCMANSMLAAVARNFN |
| TMEGd7 | -----------.-----S-D-----------------L------------------------- |
| TMEGd7 | -----------.-----S-D-----------------L------------------------- |
| TMEDa | -----------.------S---------------T--L------------C------------ |
| Vilyuisk | T----------.----L.S-DT-V-F-T------TE-L-E---T------S-----S------ |
| EMCBd | K-F--IAQI--.-I--KIP-AVP-IEA-N-.A-KTQPLAT---T-----L--TF---LS---A |
| EMCBC | K-F--IAQI--.-I--KIP-AVP-IEA-N-.A-KTQPLAT---T-----L--TF---LS---A |
| EMCDd | K-F--IAQI--.-I--KIP-AVP-IEA-N-.A-KTQPLAT---T-----L--TF---LS---A |
| EMCDc | K-F--IAQI--.-I--KIP-AVP-IEA-N-.A-KTQPLAT---T-----L--TF---LS---A |
| EMCDv1 | K-F--IAQI--.-I--KIP-AVP-IEA-N-.A-KTQPLAT---T-----L--TF---LS---A |
| EMCR | K-F--IAQI--.-I--KIP-AVP-IEA-N-.A-KTQPLAT---T-----L--TF---LS---A |
| MengoM | K-F--IAQI--.-I--KMP-AVP-IEA-N-.A-KTQPLAV---T-----L--TF---LS---A |
| Mengo37a | K-F--IAQI--.-I--KVP-AVP-IEA-N-.A-KTQPLAV---T-----L--TF---LS---A |

TABLE 3-continued

```
Ljungan   526         540                                                588
1455L     Yw---TVLKLTVYAsTFN--rLRm-fF-I.MMqG-Q-.kKHkCLfMvC-i---nt-EM-I-y.
THEBeAn   QYRGSLNFLFVFTGAAMVKGKFLIAYTPPGAGKPTTRDQAMQSTYAIWDLGLNSSFNFTAPFI
TMEGd7    ----------------------R-------------------A---------------------
TMEGd7b   ----------------------------------------- A---------------------
TMEDa     -----------------------------------------A--------------V------
Vilyuiak  ---------------S--T----------------------X---------------V---
EMCBd     ------VYT-----T--M-------------------S------A-------------YS--V---
EMCBc     ------VYT-----T--M-------------------S------A-------------YS--V---
EMCDd     ------VYT-----T--M-------------------S------A-------------YS--V---
EMCDc     ------VYT-----T--M-------------------S------A-------------YS--V---
EMCDv1    ------VYT-----T--M-------------------S------A-------------YS--V---
EMCR      ------VYT-----T--M-------------------S------A-------------YS--V---
MengoM    ------VYT-----T--M-------------------S------A-------------YS--V---
Mengo37a  ------VYT-----T--M-------------------S------A-------------YS--V---

Ljungan   589       600                                                  651
145SL     ..-.w..GnwMR--RG--I---1RiDV-NR---N-Ss-NAVnCiLQ-KM-n-AKFMv-TT-NIV-
THEBeAn   SPTHYRQTSYTSPTITSVDGWVTVWKLTPLTYPSGTPTNSDILTLVSAGDDFTLRMP.ISPTKW
TMEGd7    -------------------------Q------------------------------.------
TMEGd7b   -------------------------Q------------------------------.------
TMEDa     ------------A--A---------Q---------A-V------------------.------
Vilyuiak  --S-----------S-AA----L---Q-----F-ANV-PS----------N--------.------
EMCBd     ----F-MVGTDQVN--N--------Q-------P-C--SAK---M----K--S-K--.---AP-
EMCBc     ----F-MVGTDQ-------------Q------------------------------.------
EMCDd     ----F-MVGTDQ-------------Q------------------------------.------
EMCDc     ----F-MVGTDQ-------------Q------------------------------.------
EMCDv1    ----F-MVGTDQ-------------Q------------------------------.------
EMCR      ----F-MVGTDQ-----A-------Q------------------------------.------
MengoM    ----F-MVGTDQA------------Q------------------------------.------
Mengo37a  ----F-MVGTDL------A------Q------------------------------.------
```

Serological Assay Indicating Relationship between the Ljungan Viruses and Diabetes Mellitus and Myocarditis.

A serological assay using indirect immunofluorescence test using virus infected acetone fixed green monkey kidney cells was established. Patient sera were screened at a 1:8 dilution and positive sera titrated. Sera with a titer of 1:32 or more were considered positive.

Sera from 59 children (age 1–16) from the Stockholm area recently diagnosed with Diabetes Mellitus (DM) and 34 control children from the same geographic area, were tested for presence of antibodies to the three viruses of the invention. Nineteen of the 59 (32%) DM patients screened positive and 2 of the 34 (6%) controls were found positive to one or more of the 3 viruses (significant difference p=0.002, Fisher's exact test). Nine recently diagnosed DM patients (age 23–46) from Medelpad county were also tested. Two controls were selected for each adult DM patient and they were matched for age, sex and geographic area of residence. Five of the nine (56%) DM patients and one of the 18 (6%) control patients were found positive to one or more of the 3 viruses (significant difference p=0.008 Fisher's exact test).

Serum was also available from 5 athletes dying suddenly in myocarditis. Three controls were selected for each myocarditis patient and they were matched for age, sex and geographic area of residence. Four of the 5 (80%) patients dying from myocarditis and 1 of the 15 (7%) controls where found positive to one or more of the three Ljungan viruses (significant difference p=0.005, Fisher's exact test).

DESCRIPTION OF DIFFERENT ASPECTS OF THE INVENTION

In the following, different aspects of the invention will be disclosed. However, all of these aspects are related to a new group of picornaviruses.

Thus, a first aspect of the invention is directed to a new group of picornaviruses, namely picornaviruses comprising in their viral genome, more precisely in the non-coding region, a nucleotide sequence corresponding to a CDNA sequence selected from the group consisting of

```
SEQ ID NO: 1 (Ljungan 87-012)
AGTCTAGTCT TATCTTGTAT GTGTCCTGCA CTGAACTTGT TTCTGTCTCT 50

GGAGTGCTCT ACACTTCAGT AGGGGCTGTA CCCGGGCGGT CCCACTCTTC 100

ACAGGAATCT GCACAGGTGG CTTTCACCTC TGGACAGTGC ATTCCACACC 150

CGCTCCACGG TAGAAGATGA TGTGTGTCTT TGCTTGTGAA AAGCTTGTGA 200

AAATCGTGTG TAGGCGTAGC GGCTACTTGA GTGCCAGCGG ATTACCOCTA 250

GTGGTAACAC TAGC
``` and homologous sequences having at least 75% homology to the SEQ ID NO: 1. The picornaviruses of the invention should further cause mammalean disease.

In a preferred embodiment of this aspect of the invention said homologous sequences have at least 80%, at least 85% or at least 90% homology to the SEQ ID NO: 1.

In a particularly preferred embodiment said homologous sequence is one of

```
SEQ ID NO: 2 (Ljungan 174F)
AGTCTAGTTT CATTCTGTGT GTGTTTGGCA CTGAAATTAT TTCTGTCTCT 50

GGGGTGCTTT ACACTTCAGT AGGGGCTGTA CCCGGGCGGT CCCACTCTTC 100

ACAGGAATNT GCACAGGTGG CTTTCACCTC TGGACAGTGC ATTCCACACC 150

CGCTCCACAG TAGAAGATGA TGTGTGTCTT TGCTTGTGAA AAGCTTGTGA 200

AAATCGTGTG TAGGCGTAGC GGNTACTTGA GTGCCAGCGG ACNACCCCTA 250

GTGGTAACAC TAGC
``` and

```
SEQ ID NO: 3 (Ljungan 145SL).
AGTTTGGTTC TCTCTTGAGT GTGTTTTGTG TTAGCATAAT TTCTGTCTCT 50

AGAGTGCTTT ACACTCTAGT AGGGGCTGTA CCCGGGCGGT CCCACTCTTC 100

ACAGGAATCT GCACAGGTGG CTTTCACCTC TGGACAGTGC ATTCCATACC 150

CGCTCCACAA TAGAAGATGA TGTATATCTT TGTTTGTGAA ATGCTCATGA 200

AACGTGTGTG TAGGCGTAGC GGCTACTTGA ATGCCAGCGG AACCCCCCTA 250

GTGGTAACAC TAGC.
```

These sequences (ID NO: 2 and 3) have 94% homology and 91% homology to the SEQ ID NO: 1, respectively.

It should be understood that homologies in the coding region of different viruses of the invention may vary considerably, but in the non-coding region they share a homology of at least 75% with the SEQ ID NO: 1.

The nucleotide sequences, SEQ ID NO: 1, 2 and 3, correspond to approximately nucleotides 557–808 (a conserved region) in the genome of encephalomyelitis virus (EMCV). These three viruses have been isolated from wild rodents, more precisely bank voles. The viruses can be multiplied in cell lines, and for a large-scale production of picornavirus products the virus genome can be inserted into other microorganisms.

A second aspect of the invention is directed to a protein comprising an amino acid sequence selected from the group consisting of

```
SEQ ID NO: 4 (partial structural protein of Ljungan 145)
Lys Asp Leu Met Glu Ile Ala Arg Met Pro Ser Val Tyr Lys Gly Glu
                  5                  10                 15

Arg Thr Glu Pro Gly Gly Thr Asn Gly Tyr Phe Gln Trp Ser His Thr
             20                  25                 30

His Ser Pro Ile Asn Trp Val Phe Asp Gly Gly Ile His Leu Glu Asp
             35                  40                 45

Met Pro Asn Leu Asn Leu Phe Ser Ser Cys Tyr Asn Tyr Trp Arg Gly
         50                  55                 60

Ser Thr Val Leu Lys Leu Thr Val Tyr Ala Ser Thr Phe Asn Lys Gly
         65                  70                 75             80

Arg Leu Arg Met Ala Phe Phe Pro Ile Met Met Gln Gly Thr Gln Arg
                 85                  90                 95

Lys Lys His Lys Cys Leu Phe Met Val Cys Asp Ile Gly Leu Asn Asn
             100                 105                110

Thr Phe Glu Met Thr Ile Pro Tyr Thr Trp Gly Asn Trp Met Arg Pro
             115                 120                125

Thr Arg Gly Ser Val Ile Gly Trp Leu Arg Ile Asp Val Leu Asn Arg
         130                 135                 140

Leu Thr Tyr Asn Ser Ser Ser Pro Asn Ala Val Asn Cys Ile Leu Gln
145                 150                 155                160

Val Lys Met Gly Asn Asp Ala Lys Phe Met Val Pro Thr Thr Ser Asn
                 165                 170                175

Ile Val Trp,
``` and homologous sequences having at least 75% homology to the SEQ ID NO: 4, and antigenic fragments of the sequences.

In an embodiment of the invention the homologous sequences have at least 80%, at least 85% or at least 90% homology to the SEQ ID NO:4.

The SEQ ID NO:4 is the result of preliminary partial sequencing of the cDNA sequence from the polyprotein coding sequence of the virus Ljungan 145 SL isolate. Said protein comprising said amino acid sequence SEQ ID NO:4, said homologous sequences and said antigenic fragments are useful as active ingredients in medicines and as diagnostic reagents in diagnostic kits.

A third aspect of the invention concerns an antiserum or antibody directed against a structural protein of the virus defined in the first aspect of the invention. An example of such a structural protein is defined in the second aspect of the invention. Such an antiserum or antibody is useful as an active ingredient in medicines and as diagnostic reagent in diagnostic kits. Both polyclonal and monoclonal antibodies may be used, and these are suitably produced by using said virus or fragments thereof specific for said virus for immunizing mammals.

A fourth aspect of the invention is directed to an antigen comprising at least a part of a structural protein of the picornavirus defined in the first aspect of the invention, including a subunit thereof. An example of such an antigen is the protein and antigenic parts thereof defined in the second aspect of the invention. Such an antigen of the invention is useful as an active ingredient in medicines and as a diagnostic reagent in diagnostic kits.

A fifth aspect of the invention is directed to a diagnostic kit comprising at least one member from the group consisting of a) an antiserum or antibody according to the third aspect of the invention or an antigen-binding part thereof, b) an antigen according to the fourth aspect of the invention or an antibody-binding part thereof, c) one or several probes designed with respect to the genome of the virus according to the first aspect of the invention, and d) one or several primers designed with respect to the genome of the virus according to the first aspect of the invention.

The different members of a diagnostic kit will depend on the actual diagnostic method to be used. In addition to the above-listed possible members of the diagnostic kit, said kit may contain positive reference samples, negative reference samples, diluents, washing solutions and buffers as appropriate. The kit will further be accompanied by instructions for use.

The above-listed members a) and b) find use in immunodiagnostic methods, such as enzyme-liked immunosorbent assay (ELISA), radioimmunoassay (RIA) or immunofluorescence assay (IFA).

The above-listed members c) and d) find use in direct virus detection. Preferably, a diagnostic method based on the PCR (polymer chain reaction) technique with such primers is utilized in the direct detection of a virus according to the invention.

All of the above mentioned diagnostic methods are well known in the art, and a man of ordinary skill in the art will readily select useful members for a diagnostic kit in relation to the diagnostic method to be used.

A sixth aspect of the invention relates to a vaccine having as an immunizing or neutralizing component a member selected from the group consisting of a) the virus according to the first aspect of the invention, b) the virus according to the first aspect of the invention in attenuated form, c) the virus according to the first aspect of the invention in killed form, d) an antigen according to the fourth aspect of the invention, including a subunit of the virus according to the first aspect of the invention, and e) DNA corresponding to the genomic RNA of the virus according to the first aspect of the invention.

In an embodiment of this aspect of the invention said vaccine may additionally comprises an adjuvant. Such an adjuvant must of course be an adjuvant which is approved for use in vaccines by authorities responsible for veterinary or human medicines.

The vaccine may contain other ingredients which are needed for specific preparations intended for oral, subcutaneous, intramuscular or intradermal administration. Suitable additional ingredients are disclosed in the European or US Pharmacopoeia.

The alternative members a), b) and c) are all examples of conventional whole virus, attenuated virus, and subunit vaccines developed for other types of viruses, and the member d) represents DNA incorporation into body-specific cells, which then will express virus-specific structures and elicit immunity against said virus.

A seventh aspect of the invention is directed to a picornavirus according to the first aspect of the invention, optionally in attenuated or killed form, an antiserum or antibody according to the third aspect of the invention or an antigen according to the fourth aspect of the invention, for use in a medicament (for veterinary or human use). An example of such a medicament is a vaccine according to the invention disclosed in the sixth aspect thereof.

The eight aspect of the invention concerns use of a picornavirus according to the first aspect of the invention, optionally in attenuated or killed form, an antiserum or antibody according to the third aspect of the invention or an antigen according to the fourth aspect of the invention, in the preparation of a medicament for prophylactic or therapeutic treatment of a disease caused by said virus.

In an embodiment of said use the disease caused by said virus is one of Myocarditis, Cardiomyopathia, Guillain Barré Syndrome, and Diabetes Mellitus, Multiple Sclerosis, Chronic Fatigue Syndrome, Myasthenia Gravis, Amyothrophic Lateral Sclerosis, Dermatomyositis, Polymyositis, Spontaneous Abortion, and Sudden Infant Death Syndrome.

A ninth aspect of the invention is directed to a method of prophylactic or therapeutic treatment of a disease caused by a virus according to the first aspect of the invention in a mammal, including human, which comprises administering to said mammal a prophylactically or therapeutically effective amount of a medicament comprising as an active ingredient a member of the group consisting of a) the virus according to the first aspect of the invention, b) the virus according to the first aspect of the invention in attenuated form, c) the virus according to the first aspect of the invention in killed form, d) an antigen according to the fourth aspect of the invention, including a subunit of the virus according to the first aspect of the invention, and e) DNA corresponding to the genomic RNA of the virus according to the first aspect of the invention.

In an embodiment of said method the disease caused by said virus is one of Myocarditis, Cardiomyopathia, Guillain Barré Syndrome, and Diabetes Mellitus, Multiple Sclerosis, Chronic Fatigue Syndrome, Myasthenia Gravis, Amyothrophic Lateral Sclerosis, Dermatomyositis, Polymyositis, Spontaneous Abortion, and Sudden Infant Death Syndrome.

The actual dosage regimen will be determined by the vaccine producer based on animal experiments and clinical trials.

REFERENCES

1. Wesslén, L. et al. Myocarditis caused by *Chlamydia pneumonie* (TWAR) and sudden unexpected death in a Swedish elite orienteer. The Lancet, 340, 427–428 (1992).
2. Gard, S. Heller L. Hemagglutination by Col-MM-virus. Proc. Soc. Exp. Biol. Med. 76, 68–73 1951.
3. Francki, R. I. B., C. M. Fauquet, D. L. Knudson, and F. Brown (ed). 1991. Classification and nomenclature of viruses. Fifth report of the International Committee in Taxonomy of viruses. Arch. Virol. 1991 (Suppl. 2): 320–326.
4. Palmenberg, A. C. 1989. Sequence alignment of picornaviral capsid proteins, p. 211–241. In B. L. Semler and E. Ehrenfeld (ed.), Molecular aspects of picomavirus infection and detection. American Society for Microbiology, Washington. D.C.
5. Stanway, G. 1990. Structure, function and evolution of picornaviruses. J. Gen. Virol. 71:2483–2501.
6. Lipton, H. L., A. Friedmann, P. Sethi, and J. R. Crowther. 1983. Characterization of Vilyuisk virus as a picornavirus. J. Med. Virol. 12:195–203.
7. Zimmerman, J. J. Encephalomyocarditis. In: Handbook Series of Zoonoses. G. B. Beran (Ed.), CRC, Press Inc., Boca Raton, Fla. USA (1994).
8. Hubbard, G. B. et al. An encephalomyocarditis virus epizootic in a baboon colony. *Lab. Anim. Sci.* 42, 223–239 (1992).
9. Gaskin, J. M. et al. The tragedy of encephalomyocarditis virus infection in zoological parks in Florida. *Proc. Am. Assoc. Zoo. Vet* 1–7 (1980).
10. Craighead, J. E & McLane, M. F. Diabetes Mellitus: induction in mice by encephalomyocarditis virus. *Science* 162, 913–915 (1968).
11. Hayashi, K., Boucher, D. W. & Notkins, A. L. Virus induced diabetes mellitus. II. Relationship between-cell damage and hyperglycemia in mice infected with encephalomyocarditis virus. *Am. J. Pathol.* 75, 91–102 (1974).
12. Dal Canto, M. C. Experimental models of virus-induced demyelination, in Handbook of Multiple Sclerosis, in Cook SD (ed), New York, Marcel Decker, pp 63–100 (1990).
13. Hirasawa, K., Han, J. Takeda, M., Itagaki, S. & Doi, K. J. Encephalomyocarditis (EMC) virus induced myocarditis by different virus variants and mouse strains. *Vet. Med. Sci.* 54, 1125–1129 (1992).
14. Levin, R. et al. EMC virus infection in baboons as a model for studies on antiviral substances. *Antiviral Research* 6, 277–283 (1986).
15. Blanchard,J. L., Soike, K. & Baskin, G. B. Encephalomyocarditis virus infection in African green and squirrel monkeys: Comparison of pathologic effect. *Laboratory Animal Science* 37, 635–639 (1987).
16. Lipton, H. L. & Dal Canto, M. C. Theiler's virus induced demyelination: prevention by immunosuppression. *Science* 192, 62–64 (1976).
17. Gajdusek, D. C. Encephalomyocarditis virus infection in childhood. *Pediatrics* 16, 902–906 (1955).
18. Niklasson, B. & Le Duc, J. Epidemiology of nephropathia epidemica in Sweden. J. Inf. Dis. 155:269–276 (1987).
19. Riggs, J. L.: Immunofluorescent staining. In: Diagnostic procedures for Viral, Rickettsial, and Chiamydial infections, Am. Public. Health Assoc., Washington 1979, 5th ed., p. 141.
20. Earley, E., Peralta, P. H. & Johnson, K. M.: A plaque neutralization method for arboviruses. Proc. Soc. Exp. Biol. Med. 125:741. (1967)

The invention claimed is:

1. An isolated protein comprising SEQ ID NO:4, an amino acid sequence at least 75% homologous to SEQ ID NO:4, or an antigenic fragment of SEQ ID NO:4, wherein the antigenic fragment or the homologous sequence induces or reacts with antibodies specific to Ljungan viruses.

2. The isolated protein of claim 1, wherein the protein which comprises an antigenic fragment of SEQ ID NO:4 is at least 75% homologous to SEQ ID NO:4.

3. An immunogenic composition comprising the protein of claim 1 or claim 2.

4. The immunogenic composition of claim 3, further comprising an adjuvant.

5. An isolated antibody induced by or reactive with SEQ ID NO:4 or an antigenic fragment thereof, wherein the antibody is specific to Ljungan picornavirus, or an antigen-binding portion of said antibody.

6. The isolated antibody according to claim 5 which is polyclonal.

7. The isolated antibody according to claim 5 which is monoclonal.

8. A diagnostic kit comprising the protein of claim 1 or 2 or the antibody of claim 5, and diagnostic reagents.

9. A method of inducing an immune response in a subject comprising administering the protein according to claim 1 or 2 or the composition according to claim 3 or 4.

* * * * *

SEQUENCE LISTING

```
<160> NUMBER OF SEQ ID NOS: 20

<210> SEQ ID NO 1
<211> LENGTH: 264
<212> TYPE: DNA
<213> ORGANISM: Ljungan virus

<400> SEQUENCE: 1
agtctagtct tatcttgtat gtgtcctgca ctgaacttgt ttctgtctct ggagtgctct      60
acacttcagt aggggctgta cccgggcggt cccactcttc acaggaatct gcacaggtgg     120
ctttcacctc tggacagtgc attccacacc cgctccacgg tagaagatga tgtgtgtctt     180
tgcttgtgaa aagcttgtga aaatcgtgtg taggcgtagc ggctacttga gtgccagcgg     240
attaccccta gtggtaacac tagc                                            264

<210> SEQ ID NO 2
<211> LENGTH: 264
<212> TYPE: DNA
<213> ORGANISM: Ljungan virus
```

```
<220> FEATURE:
<221> NAME/KEY: modified_base
<222> LOCATION: (1)..(264)
<223> OTHER INFORMATION: "n" represents a, t, c, g, other or unknown

<400> SEQUENCE: 2
agtctagttt cattctgtgt gtgtttggca ctgaaattat ttctgtctct ggggtgcttt      60
acacttcagt aggggctgta cccgggcggt cccactcttc acaggaatnt gcacaggtgg     120
ctttcacctc tggacagtgc attccacacc cgctccacag tagaagatga tgtgtgtctt    180
tgcttgtgaa aagcttgtga aaatcgtgtg taggcgtagc ggntacttga gtgccagcgg    240
acnacccta gtggtaacac tagc                                              264

<210> SEQ ID NO 3
<211> LENGTH: 264
<212> TYPE: DNA
<213> ORGANISM: Ljungan virus

<400> SEQUENCE: 3
agtttggttc tctcttgagt gtgttttgtg ttagcataat ttctgtctct agagtgcttt     60
acactctagt aggggctgta cccgggcggt cccactcttc acaggaatct gcacaggtgg    120
ctttcacctc tggacagtgc attccatacc cgctccacaa tagaagatga tgtatatctt    180
tgtttgtgaa atgctcatga aacgtgtgtg taggcgtagc ggctacttga atgccagcgg    240
aaccccccta gtggtaacac tagc                                              264

<210> SEQ ID NO 4
<211> LENGTH: 179
<212> TYPE: PRT
<213> ORGANISM: Ljungan virus

<400> SEQUENCE: 4

Lys Asp Leu Met Glu Ile Ala Arg Met Pro Ser Val Tyr Lys Gly Glu
 1               5                  10                  15

Arg Thr Glu Pro Gly Gly Thr Asn Gly Tyr Phe Gln Trp Ser His Thr
             20                  25                  30

His Ser Pro Ile Asn Trp Val Phe Asp Gly Gly Ile His Leu Glu Asp
         35                  40                  45

Met Pro Asn Leu Asn Leu Phe Ser Ser Cys Tyr Asn Tyr Trp Arg Gly
     50                  55                  60

Ser Thr Val Leu Lys Leu Thr Val Tyr Ala Ser Thr Phe Asn Lys Gly
 65                  70                  75                  80

Arg Leu Arg Met Ala Phe Phe Pro Ile Met Met Gln Gly Thr Gln Arg
                 85                  90                  95

Lys Lys His Lys Cys Leu Phe Met Val Cys Asp Ile Gly Leu Asn Asn
            100                 105                 110

Thr Phe Glu Met Thr Ile Pro Tyr Thr Trp Gly Asn Trp Met Arg Pro
        115                 120                 125

Thr Arg Gly Ser Val Ile Gly Trp Leu Arg Ile Asp Val Leu Asn Arg
    130                 135                 140

Leu Thr Tyr Asn Ser Ser Pro Asn Ala Val Asn Cys Ile Leu Gln
145                 150                 155                 160

Val Lys Met Gly Asn Asp Ala Lys Phe Met Val Pro Thr Thr Ser Asn
                165                 170                 175

Ile Val Trp
```

```
<210> SEQ ID NO 5
<211> LENGTH: 241
<212> TYPE: DNA
<213> ORGANISM: Cardiovirus

<400> SEQUENCE: 5
tgacagggtt attttcacct cttcttttct actccacagt gttctatact gtggaagggt      60
atgtgttgcc ccttccttct tggagaacgt gcgcggcgt ctttccgtct ctcgacaagc     120
gcgcgtgcaa catacagagt aacgcgaaga aagcagttct cggtctagct ctagtgccca    180
caagaaaaca gctgtagcga ccacacaaag gcagcggaac ccccctcctg gtaacaggag    240
c                                                                    241

<210> SEQ ID NO 6
<211> LENGTH: 243
<212> TYPE: DNA
<213> ORGANISM: Cardiovirus

<400> SEQUENCE: 6
tgacagggtt attttc

-continued

Thr Thr Arg Asp Gln Ala Met Gln Ser Thr Tyr Ala Ile Trp Asp Leu
            100                 105                 110

Gly Leu Asn Ser Ser Phe Asn Phe Thr Ala Pro Phe Ile Ser Pro Thr
            115                 120                 125

His Tyr Arg Gln Thr Ser Tyr Thr Ser Pro Thr Ile Thr Ser Val Asp
            130                 135                 140

Gly Trp Val Thr Val Trp Lys Leu Thr Pro Leu Thr Tyr Pro Ser Gly
145                 150                 155                 160

Thr Pro Thr Asn Ser Asp Ile Leu Thr Leu Val Ser Ala Gly Asp Asp
                    165                 170                 175

Phe Thr Leu Arg Met Pro Ile Ser Pro Thr Lys Trp
            180                 185

<210> SEQ ID NO 9
<211> LENGTH: 188
<212> TYPE: PRT
<213> ORGANISM: Cardiovirus

<400> SEQUENCE: 9

Ser Asp Leu Leu Glu Leu Cys Lys Leu Pro Thr Phe Leu Gly Asn Pro
1               5                   10                  15

Ser Thr Asp Asn Lys Arg Tyr Pro Tyr Phe Ser Ala Thr Asn Ser Val
                20                  25                  30

Pro Ala Thr Ser Leu Val Asp Tyr Gln Val Ala Leu Ser Cys Ser Cys
            35                  40                  45

Met Ala Asn Ser Met Leu Ala Ala Val Ala Arg Asn Phe Asn Gln Tyr
        50                  55                  60

Arg Gly Ser Leu Asn Phe Leu Phe Val Phe Thr Gly Ala Ala Met Val
65                  70                  75                  80

Lys Gly Lys Phe Arg Ile Ala Tyr Thr Pro Pro Gly Ala Gly Lys Pro
                85                  90                  95

Thr Thr Arg Asp Gln Ala Met Gln Ala Thr Tyr Ala Ile Trp Asp Leu
            100                 105                 110

Gly Leu Asn Ser Ser Phe Asn Phe Thr Ala Pro Phe Ile Ser Pro Thr
            115                 120                 125

His Tyr Arg Gln Thr Ser Tyr Thr Ser Pro Thr Ile Thr Ser Val Asp
            130                 135                 140

Gly Trp Val Thr Val Trp Gln Leu Thr Pro Leu Thr Tyr Pro Ser Gly
145                 150                 155                 160

Thr Pro Thr Asn Ser Asp Ile Leu Thr Leu Val Ser Ala Gly Asp Asp
                    165                 170                 175

Phe Thr Leu Arg Met Pro Ile Ser Pro Thr Lys Trp
            180                 185

<210> SEQ ID NO 10
<211> LENGTH: 188
<212> TYPE: PRT
<213> ORGANISM: Cardiovirus

<400> SEQUENCE: 10

Ser Asp Leu Leu Glu Leu Cys Lys Leu Pro Thr Phe Leu Gly Asn Pro
1               5                   10                  15

Ser Thr Asp Asn Lys Arg Tyr Pro Tyr Phe Ser Ala Thr Asn Ser Val
                20                  25                  30

Pro Ala Thr Ser Leu Val Asp Tyr Gln Val Ala Leu Ser Cys Ser Cys
            35                  40                  45

```
Met Ala Asn Ser Met Leu Ala Ala Val Ala Arg Asn Phe Asn Gln Tyr
 50                  55                  60

Arg Gly Ser Leu Asn Phe Leu Phe Val Phe Thr Gly Ala Ala Met Val
 65                  70                  75                  80

Lys Gly Lys Phe Leu Ile Ala Tyr Thr Pro Pro Gly Ala Gly Lys Pro
                 85                  90                  95

Thr Thr Arg Asp Gln Ala Met Gln Ala Thr Tyr Ala Ile Trp Asp Leu
                100                 105                 110

Gly Leu Asn Ser Ser Phe Asn Phe Thr Ala Pro Phe Ile Ser Pro Thr
                115                 120                 125

His Tyr Arg Gln Thr Ser Tyr Thr Ser Pro Thr Ile Thr Ser Val Asp
                130                 135                 140

Gly Trp Val Thr Val Trp Gln Leu Thr Pro Leu Thr Tyr Pro Ser Gly
145                 150                 155                 160

Thr Pro Thr Asn Ser Asp Ile Leu Thr Leu Val Ser Ala Gly Asp Asp
                165                 170                 175

Phe Thr Leu Arg Met Pro Ile Ser Pro Thr Lys Trp
                180                 185

<210> SEQ ID NO 11
<211> LENGTH: 188
<212> TYPE: PRT
<213> ORGANISM: Cardiovirus

<400> SEQUENCE: 11

Ser Asp Leu Leu Glu Leu Cys Lys Leu Pro Thr Phe Leu Gly Asn Pro
  1               5                  10                  15

Asn Ser Asn Asn Lys Arg Tyr Pro Tyr Phe Ser Ala Thr Asn Ser Val
                 20                  25                  30

Pro Thr Thr Ser Leu Val Asp Tyr Gln Val Ala Leu Ser Cys Ser Cys
                 35                  40                  45

Met Ala Asn Ser Met Leu Ala Ala Val Ala Arg Asn Phe Asn Gln Tyr
 50                  55                  60

Arg Gly Ser Leu Asn Phe Leu Phe Val Phe Thr Gly Ala Ala Met Val
 65                  70                  75                  80

Lys Gly Lys Phe Leu Ile Ala Tyr Thr Pro Pro Gly Ala Gly Lys Pro
                 85                  90                  95

Thr Thr Arg Asp Gln Ala Met Gln Ala Thr Tyr Ala Ile Trp Asp Leu
                100                 105                 110

Gly Leu Asn Ser Ser Phe Val Phe Thr Ala Pro Phe Ile Ser Pro Thr
                115                 120                 125

His Tyr Arg Gln Thr Ser Tyr Thr Ser Ala Thr Ile Ala Ser Val Asp
                130                 135                 140

Gly Trp Val Thr Val Trp Gln Leu Thr Pro Leu Thr Tyr Pro Ser Gly
145                 150                 155                 160

Ala Pro Val Asn Ser Asp Ile Leu Thr Leu Val Ser Ala Gly Asp Asp
                165                 170                 175

Phe Thr Leu Arg Met Pro Ile Ser Pro Thr Lys Trp
                180                 185

<210> SEQ ID NO 12
<211> LENGTH: 187
<212> TYPE: PRT
<213> ORGANISM: Cardiovirus
<220> FEATURE:
<221> NAME/KEY: MOD_RES
<222> LOCATION: (102)
```

<223> OTHER INFORMATION: variable or unknown amino acid

<400> SEQUENCE: 12

```
Thr Asp Leu Leu Glu Leu Cys Lys Leu Pro Thr Phe Leu Gly Asn Leu
 1               5                  10                  15

Ser Asn Asp Thr Arg Val Pro Phe Phe Thr Ala Thr Asn Ser Val Pro
             20                  25                  30

Thr Glu Ser Leu Val Glu Tyr Gln Val Thr Leu Ser Cys Ser Cys Met
         35                  40                  45

Ser Asn Ser Met Leu Ala Ser Val Ala Arg Asn Phe Asn Gln Tyr Arg
     50                  55                  60

Gly Ser Leu Asn Phe Leu Phe Val Phe Thr Gly Ser Ala Met Thr Lys
 65                  70                  75                  80

Gly Lys Phe Leu Ile Ala Tyr Thr Pro Pro Gly Ala Gly Lys Pro Thr
                 85                  90                  95

Thr Arg Asp Gln Ala Xaa Gln Ser Thr Tyr Ala Ile Trp Asp Leu Gly
            100                 105                 110

Leu Asn Ser Ser Phe Asn Phe Thr Val Pro Phe Ile Ser Pro Ser His
        115                 120                 125

Tyr Arg Gln Thr Ser Tyr Thr Ser Pro Ser Ile Ala Ala Val Asp Gly
    130                 135                 140

Trp Leu Thr Val Trp Gln Leu Thr Pro Leu Thr Phe Pro Ala Asn Val
145                 150                 155                 160

Pro Pro Ser Ser Asp Ile Leu Thr Leu Val Ser Ala Gly Asn Asp Phe
                165                 170                 175

Thr Leu Arg Met Pro Ile Ser Pro Thr Lys Trp
            180                 185
```

<210> SEQ ID NO 13
<211> LENGTH: 187
<212> TYPE: PRT
<213> ORGANISM: Cardiovirus

<400> SEQUENCE: 13

```
Lys Asp Phe Leu Glu Ile Ala Gln Ile Pro Thr Phe Ile Gly Asn Lys
 1               5                  10                  15

Ile Pro Asn Ala Val Pro Tyr Ile Glu Ala Ser Asn Asn Ala Val Lys
             20                  25                  30

Thr Gln Pro Leu Ala Thr Tyr Gln Val Thr Leu Ser Cys Ser Cys Leu
         35                  40                  45

Ala Asn Thr Phe Leu Ala Ala Leu Ser Arg Asn Phe Ala Gln Tyr Arg
     50                  55                  60

Gly Ser Leu Val Tyr Thr Phe Val Phe Thr Gly Thr Ala Met Met Lys
 65                  70                  75                  80

Gly Lys Phe Leu Ile Ala Tyr Thr Pro Pro Gly Ala Gly Lys Pro Thr
                 85                  90                  95

Ser Arg Asp Gln Ala Met Gln Ala Thr Tyr Ala Ile Trp Asp Leu Gly
            100                 105                 110

Leu Asn Ser Ser Tyr Ser Phe Thr Val Pro Phe Ile Ser Pro Thr His
        115                 120                 125

Phe Arg Met Val Gly Thr Asp Gln Val Asn Ile Thr Asn Val Asp Gly
    130                 135                 140

Trp Val Thr Val Trp Gln Leu Thr Pro Leu Thr Tyr Pro Pro Gly Cys
145                 150                 155                 160

Pro Thr Ser Ala Lys Ile Leu Thr Met Val Ser Ala Gly Lys Asp Phe
```

```
                      165                 170                 175

Ser Leu Lys Met Pro Ile Ser Pro Ala Pro Trp
            180                 185

<210> SEQ ID NO 14
<211> LENGTH: 187
<212> TYPE: PRT
<213> ORGANISM: Cardiovirus

<400> SEQUENCE: 14

Lys Asp Phe Leu Glu Ile Ala Gln Ile Pro Thr Phe Ile Gly Asn Lys
  1               5                  10                  15

Ile Pro Asn Ala Val Pro Tyr Ile Glu Ala Ser Asn Asn Ala Val Lys
             20                  25                  30

Thr Gln Pro Leu Ala Thr Tyr Gln Val Thr Leu Ser Cys Ser Cys Leu
         35                  40                  45

Ala Asn Thr Phe Leu Ala Ala Leu Ser Arg Asn Phe Ala Gln Tyr Arg
     50                  55                  60

Gly Ser Leu Val Tyr Thr Phe Val Phe Thr Gly Thr Ala Met Met Lys
 65                  70                  75                  80

Gly Lys Phe Leu Ile Ala Tyr Thr Pro Pro Gly Ala Gly Lys Pro Thr
                 85                  90                  95

Ser Arg Asp Gln Ala Met Gln Ala Thr Tyr Ala Ile Trp Asp Leu Gly
            100                 105                 110

Leu Asn Ser Ser Tyr Ser Phe Thr Val Pro Phe Ile Ser Pro Thr His
        115                 120                 125

Phe Arg Met Val Gly Thr Asp Gln Pro Thr Ile Thr Ser Val Asp Gly
    130                 135                 140

Trp Val Thr Val Trp Gln Leu Thr Pro Leu Thr Tyr Pro Ser Gly Thr
145                 150                 155                 160

Pro Thr Asn Ser Asp Ile Leu Thr Leu Val Ser Ala Gly Asp Asp Phe
                165                 170                 175

Thr Leu Arg Met Pro Ile Ser Pro Thr Lys Trp
            180                 185

<210> SEQ ID NO 15
<211> LENGTH: 187
<212> TYPE: PRT
<213> ORGANISM: Cardiovirus

<400> SEQUENCE: 15

Lys Asp Phe Leu Glu Ile Ala Gln Ile Pro Thr Phe Ile Gly Asn Lys
  1               5                  10                  15

Ile Pro Asn Ala Val Pro Tyr Ile Glu Ala Ser Asn Thr Ala Val Lys
             20                  25                  30

Thr Gln Pro Leu Ala Thr Tyr Gln Val Thr Leu Ser Cys Ser Cys Leu
         35                  40                  45

Ala Asn Thr Phe Leu Ala Ala Leu Ser Arg Asn Phe Ala Gln Tyr Arg
     50                  55                  60

Gly Ser Leu Val Tyr Thr Phe Val Phe Thr Gly Thr Ala Met Met Lys
 65                  70                  75                  80

Gly Lys Phe Leu Ile Ala Tyr Thr Pro Pro Gly Ala Gly Lys Pro Thr
                 85                  90                  95

Ser Arg Asp Gln Ala Met Gln Ala Thr Tyr Ala Ile Trp Asp Leu Gly
            100                 105                 110

Leu Asn Ser Ser Tyr Ser Phe Thr Val Pro Phe Ile Ser Pro Thr His
```

```
                     115                 120                 125
Phe Arg Met Val Gly Thr Asp Gln Pro Thr Ile Thr Ser Val Asp Gly
    130                 135                 140

Trp Val Thr Val Trp Gln Leu Thr Pro Leu Thr Tyr Pro Ser Gly Thr
145                 150                 155                 160

Pro Thr Asn Ser Asp Ile Leu Thr Leu Val Ser Ala Gly Asp Asp Phe
                165                 170                 175

Thr Leu Arg Met Pro Ile Ser Pro Thr Lys Trp
            180                 185

<210> SEQ ID NO 16
<211> LENGTH: 187
<212> TYPE: PRT
<213> ORGANISM: Cardiovirus

<400> SEQUENCE: 16

Lys Asp Phe Leu Glu Ile Ala Gln Ile Pro Thr Phe Ile Gly Asn Lys
  1               5                  10                  15

Ile Pro Asn Ala Val Pro Tyr Ile Glu Ala Ser Asn Asn Ala Val Lys
                 20                  25                  30

Thr Gln Pro Leu Ala Thr Tyr Gln Val Thr Leu Ser Cys Ser Cys Leu
             35                  40                  45

Ala Asn Thr Phe Leu Ala Ala Leu Ser Arg Asn Phe Ala Gln Tyr Arg
         50                  55                  60

Gly Ser Leu Val Tyr Thr Phe Val Phe Thr Gly Thr Ala Met Met Lys
 65                  70                  75                  80

Gly Lys Phe Leu Ile Ala Tyr Thr Pro Pro Gly Ala Gly Lys Pro Thr
                 85                  90                  95

Ser Arg Asp Gln Ala Met Gln Ala Thr Tyr Ala Ile Trp Asp Leu Gly
            100                 105                 110

Leu Asn Ser Ser Tyr Ser Phe Thr Val Pro Phe Ile Ser Pro Thr His
        115                 120                 125

Phe Arg Met Val Gly Thr Asp Gln Pro Thr Ile Thr Ser Val Asp Gly
    130                 135                 140

Trp Val Thr Val Trp Gln Leu Thr Pro Leu Thr Tyr Pro Ser Gly Thr
145                 150                 155                 160

Pro Thr Asn Ser Asp Ile Leu Thr Leu Val Ser Ala Gly Asp Asp Phe
                165                 170                 175

Thr Leu Arg Met Pro Ile Ser Pro Thr Lys Trp
            180                 185

<210> SEQ ID NO 17
<211> LENGTH: 187
<212> TYPE: PRT
<213> ORGANISM: Cardiovirus

<400> SEQUENCE: 17

Lys Asp Phe Leu Glu Ile Ala Gln Ile Pro Thr Phe Ile Gly Asn Lys
  1               5                  10                  15

Ile Pro Asn Ala Val Pro Tyr Ile Glu Ala Ser Asn Asn Ala Val Lys
                 20                  25                  30

Thr Gln Pro Leu Ala Thr Tyr Gln Val Thr Leu Ser Cys Ser Cys Leu
             35                  40                  45

Ala Asn Thr Phe Leu Ala Ala Leu Ser Arg Asn Phe Ala Gln Tyr Arg
         50                  55                  60

Gly Ser Leu Val Tyr Thr Phe Val Phe Thr Gly Thr Ala Met Met Lys
```

```
               65                  70                  75                  80
Gly Lys Phe Leu Ile Ala Tyr Thr Pro Gly Ala Gly Lys Pro Thr
                        85                  90                  95

Ser Arg Asp Gln Ala Met Gln Ala Thr Tyr Ala Ile Trp Asp Leu Gly
                100                 105                 110

Leu Asn Ser Ser Tyr Ser Phe Thr Val Pro Phe Ile Ser Pro Thr His
                115                 120                 125

Phe Arg Met Val Gly Thr Asp Gln Pro Thr Ile Thr Ser Val Asp Gly
            130                 135                 140

Trp Val Thr Val Trp Gln Leu Thr Pro Leu Thr Tyr Pro Ser Gly Thr
145                 150                 155                 160

Pro Thr Asn Ser Asp Ile Leu Thr Leu Val Ser Ala Gly Asp Asp Phe
                    165                 170                 175

Thr Leu Arg Met Pro Ile Ser Pro Thr Lys Trp
                180                 185

<210> SEQ ID NO 18
<211> LENGTH: 187
<212> TYPE: PRT
<213> ORGANISM: Cardiovirus

<400> SEQUENCE: 18

Lys Asp Phe Leu Glu Ile Ala Gln Ile Pro Thr Phe Ile Gly Asn Lys
  1               5                  10                  15

Ile Pro Asn Ala Val Pro Tyr Ile Glu Ala Ser Asn Asn Ala Val Lys
                 20                  25                  30

Thr Gln Pro Leu Ala Thr Tyr Gln Val Thr Leu Ser Cys Ser Cys Leu
             35                  40                  45

Ala Asn Thr Phe Leu Ala Ala Leu Ser Arg Asn Phe Ala Gln Tyr Arg
         50                  55                  60

Gly Ser Leu Val Tyr Thr Phe Val Phe Thr Gly Thr Ala Met Met Lys
 65                  70                  75                  80

Gly Lys Phe Leu Ile Ala Tyr Thr Pro Pro Gly Ala Gly Lys Pro Thr
                     85                  90                  95

Ser Arg Asp Gln Ala Met Gln Ala Thr Tyr Ala Ile Trp Asp Leu Gly
                100                 105                 110

Leu Asn Ser Ser Tyr Ser Phe Thr Val Pro Phe Ile Ser Pro Thr His
            115                 120                 125

Phe Arg Met Val Gly Thr Asp Gln Pro Thr Ile Thr Ser Ala Asp Gly
        130                 135                 140

Trp Val Thr Val Trp Gln Leu Thr Pro Leu Thr Tyr Pro Ser Gly Thr
145                 150                 155                 160

Pro Thr Asn Ser Asp Ile Leu Thr Leu Val Ser Ala Gly Asp Asp Phe
                    165                 170                 175

Thr Leu Arg Met Pro Ile Ser Pro Thr Lys Trp
                180                 185

<210> SEQ ID NO 19
<211> LENGTH: 187
<212> TYPE: PRT
<213> ORGANISM: Cardiovirus

<400> SEQUENCE: 19

Lys Asp Phe Leu Glu Ile Ala Gln Ile Pro Thr Phe Ile Gly Asn Lys
  1               5                  10                  15

Met Pro Asn Ala Val Pro Tyr Ile Glu Ala Ser Asn Asn Ala Val Lys
```

-continued

```
                    20                  25                  30
Thr Gln Pro Leu Ala Val Tyr Gln Val Thr Leu Ser Cys Ser Cys Leu
            35                  40                  45

Ala Asn Thr Phe Leu Ala Ala Leu Ser Arg Asn Phe Ala Gln Tyr Arg
        50                  55                  60

Gly Ser Leu Val Tyr Thr Phe Val Phe Thr Gly Thr Ala Met Met Lys
65                  70                  75                  80

Gly Lys Phe Leu Ile Ala Tyr Thr Pro Pro Gly Ala Gly Lys Pro Thr
                85                  90                  95

Ser Arg Asp Gln Ala Met Gln Ala Thr Tyr Ala Ile Trp Asp Leu Gly
            100                 105                 110

Leu Asn Ser Ser Tyr Ser Phe Thr Val Pro Phe Ile Ser Pro Thr His
            115                 120                 125

Phe Arg Met Val Gly Thr Asp Gln Ala Thr Ile Thr Ser Val Asp Gly
        130                 135                 140

Trp Val Thr Val Trp Gln Leu Thr Pro Leu Thr Tyr Pro Ser Gly Thr
145                 150                 155                 160

Pro Thr Asn Ser Asp Ile Leu Thr Leu Val Ser Ala Gly Asp Asp Phe
                165                 170                 175

Thr Leu Arg Met Pro Ile Ser Pro Thr Lys Trp
            180                 185
```

<210> SEQ ID NO 20
<211> LENGTH: 187
<212> TYPE: PRT
<213> ORGANISM: Cardiovirus

<400> SEQUENCE: 20

```
Lys Asp Phe Leu Glu Ile Ala Gln Ile Pro Thr Phe Ile Gly Asn Lys
1               5                   10                  15

Val Pro Asn Ala Val Pro Tyr Ile Glu Ala Ser Asn Asn Ala Val Lys
                20                  25                  30

Thr Gln Pro Leu Ala Val Tyr Gln Val Thr Leu Ser Cys Ser Cys Leu
            35                  40                  45

Ala Asn Thr Phe Leu Ala Ala Leu Ser Arg Asn Phe Ala Gln Tyr Arg
        50                  55                  60

Gly Ser Leu Val Tyr Thr Phe Val Phe Thr Gly Thr Ala Met Met Lys
65                  70                  75                  80

Gly Lys Phe Leu Ile Ala Tyr Thr Pro Pro Gly Ala Gly Lys Pro Thr
                85                  90                  95

Ser Arg Asp Gln Ala Met Gln Ala Thr Tyr Ala Ile Trp Asp Leu Gly
            100                 105                 110

Leu Asn Ser Ser Tyr Ser Phe Thr Val Pro Phe Ile Ser Pro Thr His
            115                 120                 125

Phe Arg Met Val Gly Thr Asp Leu Pro Thr Ile Thr Ser Ala Asp Gly
        130                 135                 140

Trp Val Thr Val Trp Gln Leu Thr Pro Leu Thr Tyr Pro Ser Gly Thr
145                 150                 155                 160

Pro Thr Asn Ser Asp Ile Leu Thr Leu Val Ser Ala Gly Asp Asp Phe
                165                 170                 175

Thr Leu Arg Met Pro Ile Ser Pro Thr Lys Trp
            180                 185
```